(12) United States Patent
Courtois et al.

(10) Patent No.: US 7,897,390 B2
(45) Date of Patent: Mar. 1, 2011

(54) CELL CULTURE SYSTEM

(75) Inventors: Didier Courtois, St. Avertin (FR); Robert Gilles Arnaud Cuvier, Chambray-les-Tours (FR); Nicolas Henault, Sezanne (FR)

(73) Assignee: Nestec S.A., Vevey (CH)

( * ) Notice: Subject to any disclaimer, the term of this patent is extended or adjusted under 35 U.S.C. 154(b) by 869 days.

(21) Appl. No.: 10/595,888

(22) PCT Filed: Nov. 18, 2004

(86) PCT No.: PCT/EP2004/013082

§ 371 (c)(1), (2), (4) Date: May 18, 2006

(87) PCT Pub. No.: WO2005/049785

PCT Pub. Date: Jun. 2, 2005

(65) Prior Publication Data

US 2007/0037279 A1  Feb. 15, 2007

(30) Foreign Application Priority Data

Nov. 18, 2003 (EP) ................................. 03026377

(51) Int. Cl.
*C12N 5/02* (2006.01)

(52) U.S. Cl. ..................................... 435/393; 435/295.2

(58) Field of Classification Search ........................ None
See application file for complete search history.

(56) References Cited

U.S. PATENT DOCUMENTS

| 4,136,970 A | 1/1979 | Cabrera et al. |
| 4,649,117 A | 3/1987 | Familletti |
| 5,057,429 A | 10/1991 | Watanabe et al. |
| 5,225,346 A | 7/1993 | Matsumiya et al. |
| 6,190,913 B1 | 2/2001 | Singh |
| 6,432,698 B1 | 8/2002 | Gaugler et al. |

FOREIGN PATENT DOCUMENTS

WO  WO 85/03458 A1 *  8/1985

* cited by examiner

*Primary Examiner*—James S Ketter
(74) *Attorney, Agent, or Firm*—K&L Gates LLP

(57) ABSTRACT

The present invention provides a novel apparatus to grow cells where the cultivation chamber (1) is partially filled with liquid cultivation medium and cells. Mixing and aeration is achieved by generating intermittently one single large gas bubble (6) at the bottom of the column bioreactor, the single large bubble width representing from 50 to 99% of the tank width, preferably from 60 to 99%, more preferably 98.5%. The culture medium flows out as a film between the large bubble and the inner wall of the bioreactor. This rising bubble allows mixing and aeration of the bulk. As the design of the invention is very simple, it is possible to manufacture it with flexible plastic material and use the apparatus as a disposable system. Moreover, such a mixing/aeration principle minimizes cell damages usually due to shear stress and small bubbles and allows easy and efficient scale-up from small scale to a larger one. Such a large-scale, efficient and disposable culture system can largely reduce production costs.

5 Claims, 4 Drawing Sheets

CELL CULTURE SYSTEM

FIELD OF THE INVENTION

The present invention relates to the field of cell culture. This invention provides a new culture system, for growing cells in general and plant cells in particular. Since this apparatus can be disposable and efficient at large scale, its use allows a great reduction of production costs in different kinds of applications.

BACKGROUND OF THE INVENTION

Conventional culture systems are generally composed of a rigid container (glass or stainless steel) having a means for aerating and mixing the culture content (air sparger, impeller). These systems are complex, and usual equipment and support facilities associated with aseptic bioprocess are extremely expensive because the large-scale production is based on stainless steel vessels, sterilized in situ. More than 60% of the production costs is due to the fixed costs: high capital costs of fermentation equipment, depreciation, interest and capital expenditure. The running costs are also high, due to low yields and the needs to clean and sterilize the bioreactor after each culturing cycle. In the particular industrial application of plant cell cultures, different well-known culture systems have been used such as stirred tank or airlift reactors. Despite many efforts to commercialise plant metabolites, few achieved commercial success. One reason is the low productivity in spite of the possibility to obtain higher content of desired compound than in whole plant (rosmarinic acid, shikonin, etc.), up to 20% of dry weight. The main constraint leading to a low productivity remains the low growth rate (below 0.7 day$^{-1}$, min 20 h doubled-time) compared to bacteria. Using batch culture in industrial fermentor means to operate no more than 10-20 runs per year with plant cell cultures in very high cost facilities. It means that the bottleneck for an industrial production is more an economical one than a biological one.

To overcome these problems and decrease production costs, new technologies recently appeared, based on the use of various disposable plastic bags instead of stainless steel fermentor. These new systems using pre-sterile disposable plastic bags are promising because they decrease capital investment since plastic is a low cost material and moreover they eliminate cleaning, sterilization, validation and maintenance of equipment, which is time and cost consuming. It also allows more flexibility in the process, which can be operated by people not skilled in the art since bags are provided pre-sterile.

Different aeration/mixing systems have been proposed in such disposable apparatus. Wave Biotech (Singh V, U.S. Pat. No. 6,190,913) has developed a system using an inflated bag placed on a rocking mechanism that moves the bag inducing a wave-like motion to the liquid contained therein. The rocking mechanism limits the size of the tank because such a mechanical agitation needs complex equipment to reach high volumes of culture.

Another suggestion is to use gas permeable plastic bags agitated with a mechanical system or not agitated at all. In U.S. Pat. No. 5,057,429 a gas permeable bag is rotated or shaked to diffuse oxygen and nutrients to the animal cells. A static gas-permeable bag is also described in U.S. Pat. No. 5,225,346. Up to now there is no industrial development of such culture systems mostly because on one hand there is a difficulty to scale-up an external agitation apparatus and on the other hand there are problems due to insufficient oxygen supply to the cells in a static bag containing several liters of culture medium.

A reactor can consist of a gas-sparged plastic bag in a tank with a head plate that has capabilities for inoculation and media sample removal. Disposable conical plastic bags produced by Osmotec are for small-scale use (few liters), using air bubbles for aeration through an inlet. U.S. Pat. No. 6,432,698 also describes a disposable bioreactor for culturing microorganisms or cells, comprising a gas bubbler, generating gas bubbles for mixing and providing gases, close to airlift bioreactor except it is herein made in plastic material.

In these inventions, there are two main constraints: at high density or high volumes of culture, there is a need to create smaller gas bubbles or fluid circulation in the whole reactor to achieve convenient mixing and aeration. This results in complex bubbling systems (gas diffusers, partitioned tanks . . .), which are not in agreement with a simple disposable technology. Moreover, small bubbles are detrimental to sensitive cells, increase cell to wall adhesion and/or strip off some useful gases from the culture medium (ethylene for plant cell for example).

The use of gas bubbles for the aeration of bioreactor or fermenter is well known. Currently a diffuser injecting microbubbles is used to improved the gas transfer into the culture medium. Bioreactor where the aeration and also agitation is done through gas stream without mechanical agitation is also well known and currently named airlift bioreactor by the specialists. For example, U.S. Pat. No. 4,649,117 describes the culture system of airlift bioreactor, useful for carrying out cell culture and fermentation. Suitable gas flow rate are in the range of 10 to 300 cc/min, and the gas is gently continuously bubbled, without any reference to the size of bubbles or the periodic generation of single large bubble as in our present invention. Two chambers are used, a growth chamber and a mixing chamber.

The use of single bubble, noted as "large" but inferior to 3 cm$^3$, is known for mixing and blending various materials such as chemicals, beverages or oils. WO-A-8503458 describes a method and apparatus for gas induced mixing and blending, not concerning the growth and cultivation of living cells. The method is based on gas bubbles of predetermined variable size and frequency injected into a tank through one or several air inlets. The goals are to reduce overall blending and mixing time, which is not the one of our present invention. The injection is done to obtain a single bubble or several single bubbles, the size of the bubble and the quantity of air being an empirical determination, and the bubble should not being too large (1 cubic inch (2.54 cm$^3$) cited), not being specifically a bubble with a diameter close to the one of the tank. This is quite different from our present invention where the size of the bubble and quantity of air is critical for the growth of the living cells. In WO-A-8503458, in case of several air inlets, several single bubbles are generated to have circular, vertical toroidal flow patterns. WO-A-8503458 invention is used for open or vented tanks, which is not compatible with the cultivation of living cells under sterile conditions.

U.S. Pat. No. 4,136,970 describes also a method and apparatus for regulating the size and frequency of bubbles employed for mixing liquids. It does not concern itself with the oxygenation and cultivation of living cells, not concern with maximising the size of the bubbles, and does not concern with large bubble higher than 1.5 cm$^3$. The method described in U.S. Pat. No. 4,136,970 can be used for the counting of blood platelets but can in no case adapted, used or claimed for the cultivation and growing of living cells.

The aim of the present invention is to provide a low cost cell culture system via a disposable apparatus, which is efficient at large scale and easy to use.

SUMMARY OF THE INVENTION

The present invention consists in a pre-sterilized flexible or non flexible plastic bag in which cells are cultivated, being agitated/aerated by single large gas-bubble.

In the present invention, a single large gas-bubble is generated intermittently at the bottom of the column, partially filled with liquid medium and cells. As the large bubble almost fills the cross-section of the column, it creates a thin space between the bubble and the sidewalls of the cylindrical tank where the liquid can flow as the bubble rises. This trickling liquid film, in contact with gas-bubble, allows convenient mixing and aeration of the bulk in the apparatus during operation without damaging the cells. Such a mixing/aeration system allows an efficient scale-up since oxygen and mass transfer reactions occur at the thin liquid film level. Moreover, as the system is simply designed, capital and maintenance costs are greatly reduced.

This disposable apparatus is made of sterilizable and flexible plastic sheets sealed along their edges to form a column. Such a disposable system allows process flexibility and decreases dead time since no cleaning, sterilization, maintenance or validation are required like in traditional stainless steel devices.

As the present invention is disposable and efficient at large scale, it is a good alternative system to decrease production costs in industrial applications.

This culture system can be applied for plant, animal, insect or micro-organism cultures, in suspension or immobilized on different carrier systems. The process allows to produce a large variety of molecules like metabolites (de novo or via biotransformation) or recombinant proteins, or to multiply embryogenic plant cell line through batch, fed-batch or continuous culture, as well as any other use that could be obvious for the skilled person.

DETAILED DESCRIPTION OF THE INVENTION

The present invention consists in the use of very large single bubbles, periodically produced (whatever the process to obtain them), having a diameter as close as possible from the one of the bioreactor itself for the aeration/agitation (providing a efficient oxygenation) of cell cultures. The consequence is that the culture medium flows out as a very thin film between the large bubble and the inner wall of the bioreactor.

Figure 1:
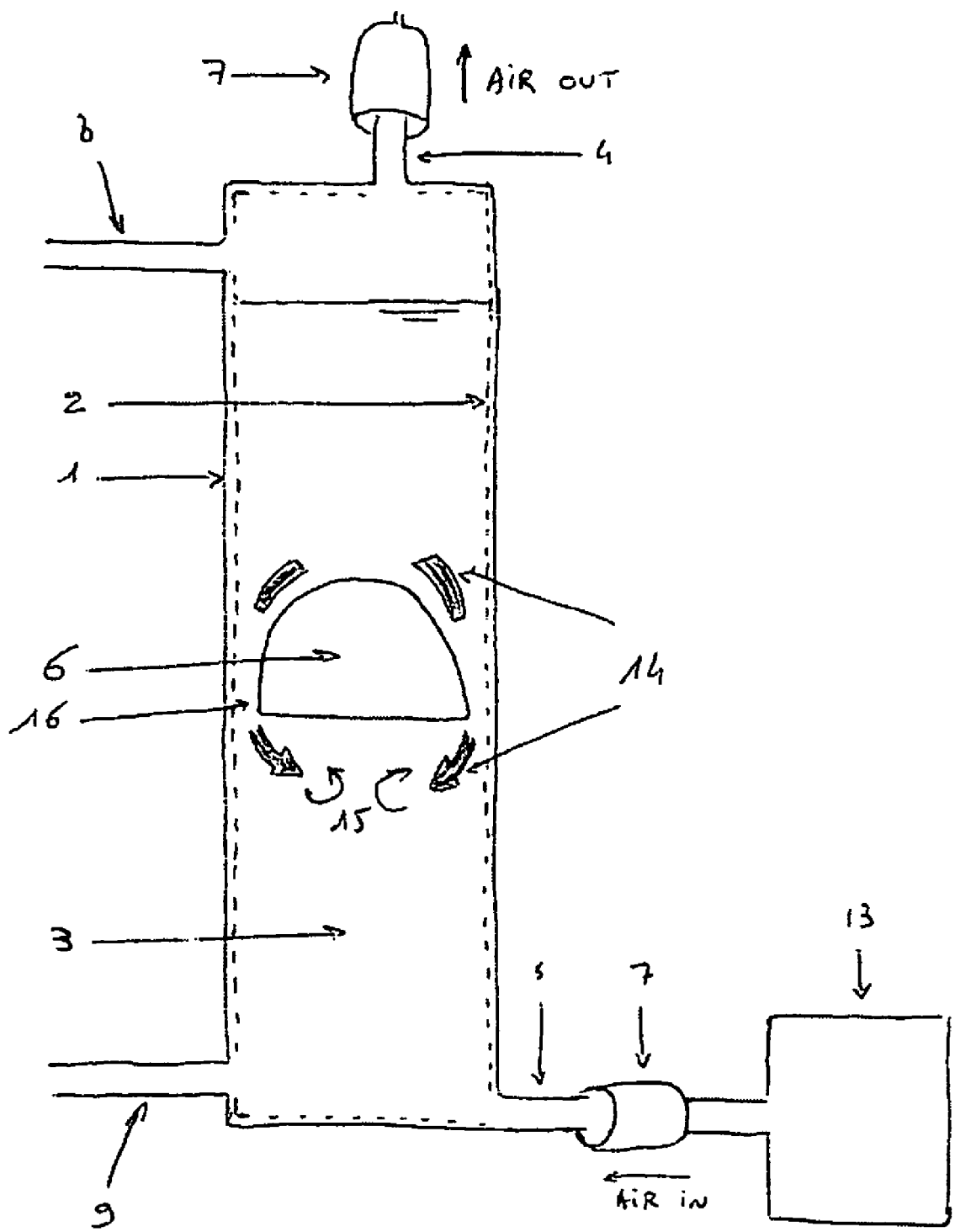
FIG. 1 is a side view of the apparatus, showing the bag and phenomena created by the rising bubble.

In a basic design, as shown in FIG. 1, the bioreactor (or reactor) is composed of different parts, comprising at least one tank (1) made of material, such as plastic sheets sealed along their edges (2), for example, to create an interior. The tank is stationary. In a preferred embodiment of the present invention, the tank(s) are made of flexible polypropylene for its sealable and autoclavable properties, so it can be sterilized in a small laboratory autoclave or by any other means well known in the art. However other kinds of materials are also suitable such as Pyrex®, stainless-steel, semi-flexible, rigid or molded plastics, among others and can be sterilized by any method known by people skilled in the art such as gamma radiation.

In a preferred embodiment of the invention, flexible biocompatible water proof material are heat-sealed along their edges (2), for example, with a thermic impulse sealer. However other sealing techniques can also be used, in accordance with methods well known in the art including, but not limited to, ultrasound or radio wave welding. Other kinds of plastics can be manufactured in a different manner such as mold injection for example.

In the present invention, as shown in FIG. 1, the reactor can be cylindrical or can have an oval cross section, it can have 2 m height and its diameter can be 12 cm for a working volume of 20 liters.

Smaller or higher volumes can be used according to the present invention. For example, the diameter of the reactor can be as small as 5 cm and can go up to 40 cm or more. The height of the reactor can vary according to the needs of the user and the diameter chosen.

The reactor can also have different shapes but preferably the height of the shape is at least 5 times its width. It can be, for example a parallelepiped. The dimensions and shape of the tank (1) can be varied to suit the needs of the users; however, the cylindrical column shape is preferred. It is important to avoid dead space, where mixing does not occur, when culturing cells in suspension. Dead spaces appear preferentially at the corners, that's why it is preferred to manufacture rounded-bottoms mostly with cells, which tend to form dense aggregates (such as plant cells), which settle more rapidly than individual cells.

If the tank is made in a flexible matter, such as plastic, it is recommended to put the said tank in a rigid outer container to support shape and weight of the tank. This rigid container can be made of any material such as polycarbonate but this material will be chosen mostly for its rigidity and strength properties (assumed by thickness and/or formulation). This outer container can be translucent to facilitate observation of the culture (3) if the plastic bag is also translucent or to improve light transmission when growing photoautotrophic cells for example. Dimensions and shapes of outer containers are preferably designed according to dimensions and shapes of tank discussed above.

In the basic design shown in FIG. 1, at least four tubes are connected to the tank. The first one, at the top, is used to remove excess of gases (4). The second one, at the bottom of the tank (5), is used to provide air to the liquid culture through gas-bubble (6). These tubes are equipped, in the most preferred embodiment, with filters (7), such as for example 0.22 μm filters, to prevent airborne contamination. Air inlet tubing can be equipped with a valve to prevent back flush of the liquid in the tube. Moreover, one inlet tube (8) located at the top of the tank allows to fill the bioreactor with sterile medium and inoculum and one outlet tube (9) located nearby the bottom may be needed to harvest and/or sample the culture bulk.

In a preferred embodiment, tubing is semi-flexible, made of autoclavable silicone but other types of tubing like C-flex or PVC can also be used. In the preferred embodiment of the present invention, inner diameters of tubing are 8 mm, except for air inlet tubing which is larger: 11 mm diameter. Lengths of tubing are about one to two meter in this invention but users, to meet requirements, can adjust these dimensions.

Figure 2:
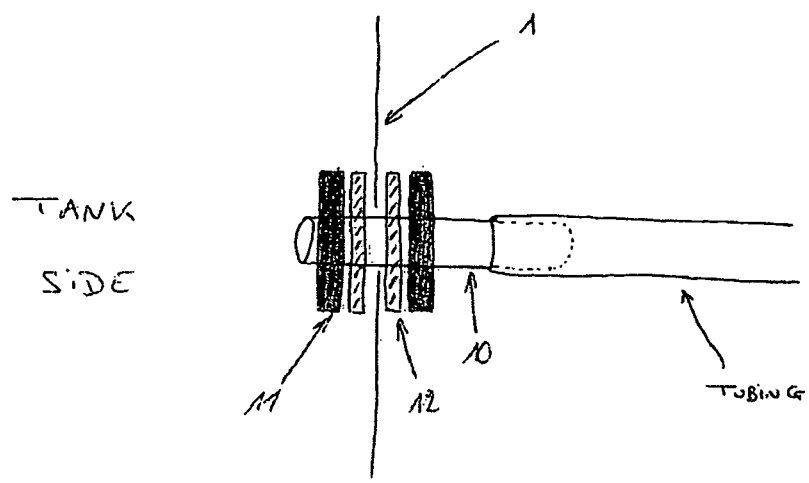
FIG. 2 is a side view of plastic bag to tubing connection.

Tubing can be connected to the tank via an incorporation port welded on the plastic sheet according to standard techniques such as heat-sealing. In the preferred embodiment of the present invention, as shown in FIG. 2, tubing is connected to the tank through a hole in the plastic sheet to autoclavable panel mount union (10) equipped with bolts (11) and seams (12). Imperviousness can be obtained by screwing bolts to clench seams on the plastic sheet. Inner diameters of panel mount union are equal to inner diameters of corresponding tubings in this invention but it is possible to adjust dimensions as needed.

However, it has to be understood that any means allowing air or gas to circulate can be adapted to the present invention. It is important, for the purpose of the present invention, that aeration and mixing of the medium is achieved by large gas/air bubbles, and preferably by a single large bubble created every few seconds, having its diameter dictated by the diameter of the tank. Consequently the preferred mixing and aeration means of the invention consists in a bubble that is more long than wide. However, the system also works when bubbles are as long as wide.

Preferably, the large bubble shape is dictated by the shape of the tank; in other words, the space between the bubble and the tank is restricted to a minimum: to a film of medium comprising cells. Preferably, the culture medium flows out as a very thin film between the large bubble and the inner wall of the bioreactor. However, the system also works when the film is less thin and the bubble represents from 50 to 99% of the width of the tank preferably from 60 to 99%, more preferably 98.5%.

By large bubbles, it has to be understood that the volume of each single and large bubble is at least of 65 cm$^3$, more preferably of at least 500 cm$^3$. For example, in reactors having a diameter of around 20 cm, preferred volumes for the large bubbles can vary between 2600 and 4100 cm$^3$, or more preferably between 3000 and 4100 cm$^3$, or even more preferably between 3500 or 3700 and 4100 cm$^3$.

Figure 3:
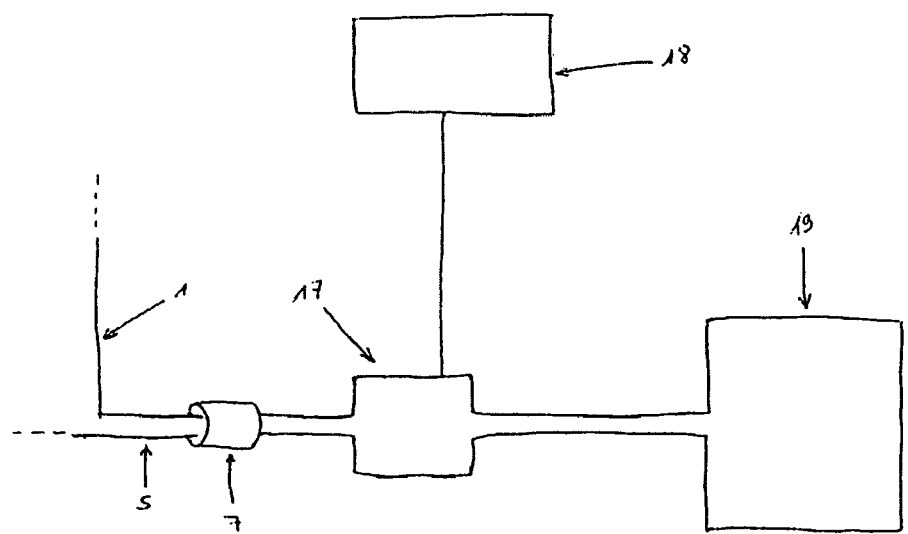
FIG. 3 is a schematic of the pneumatic and electric circuits useful for generation and control of the frequency and size of bubbles.

To create large bubbles, a bubble generator (13) is linked to the air inlet tube. The bubble generator, as shown in FIG. 3, is for example, an electro-gate (17), controlled by a timer (18) and linked to a gas pump (19). In such a configuration, the electro-gate, controlled electrically by the timer, is directly linked to air inlet and gas pump. Regularly, the timer (programmed by users) sends an electrical signal to the electro-gate for a very short period of time. During this time, the electro-gate is open and allows gas supplied from the pump to enter the bioreactor. When a high flow of gas is supplied for a very short period of time in the column, it creates a single large bubble, which fills almost the cross section of the column. In the present invention, section of the electro-gate is 15 mm, air pressure at the gas pump is 0.5 bar and the electrical signal, during 0.1 second, is sent every 5 seconds, thus creating a large bubble every 5 seconds. Users, depending on their needs, can adjust these parameters.

Figure 4:
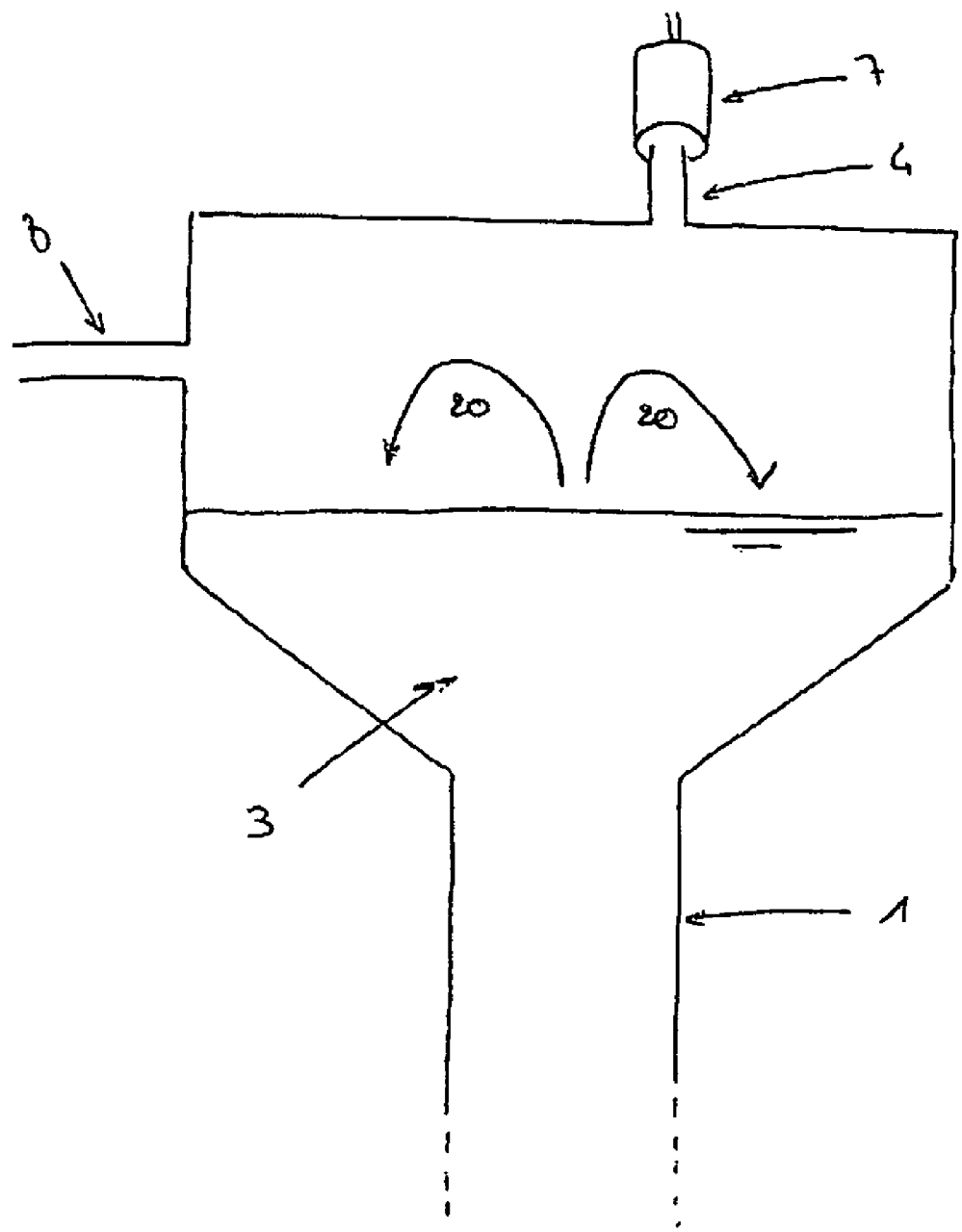
FIG. 4 shows top of the upper part of the tank in the form of an inversed cone.
Figure 5:
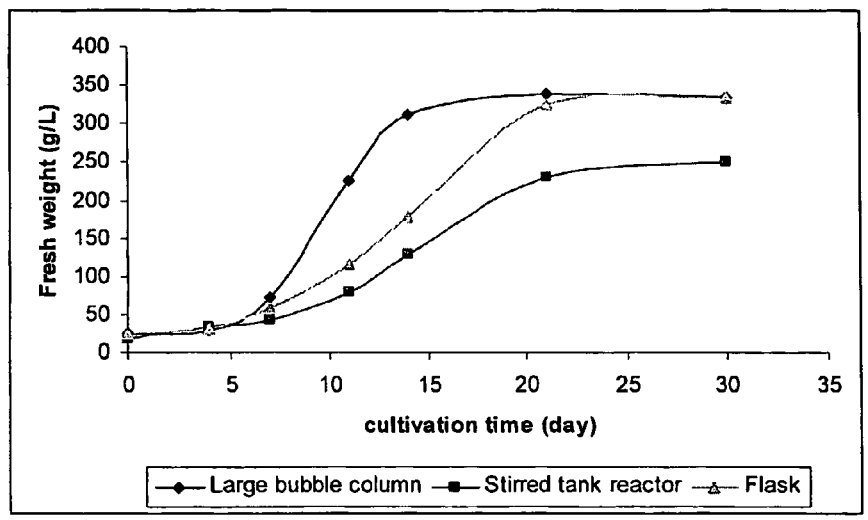
FIG. 5 shows growth kinetics of Soya cells in flasks, stirred tank reactor and Cell culture system, expressed in fresh weight per liter of liquid culture.
Figure 6:
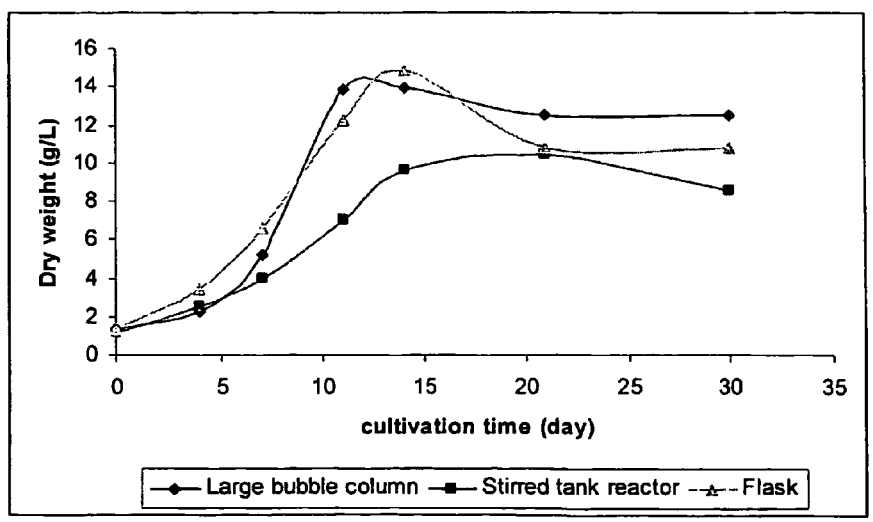
FIG. 6 shows growth kinetics of Soya cells in flasks, stirred tank reactor and Cell culture system, expressed in dry weight per liter of liquid culture.

This kind of bubble generator is preferred but other devices allowing creation of a large gas bubble in the column can also be used. In the present invention, the gas used is air but other gases alone or mixed or recycled from the bioreactor can be used to meet the requirements of the cells, for example $CO_2$ for photoautotrophic plant cells. When the bubble arrives at the top of the column, is somehow explodes, and some medium/cells can be lost on the walls of the tank (1). To avoid this disadvantage, in an embodiment of the present invention, the upper part of the tank is flared, for example in the preferred embodiment it is in the form of an inversed cone, so that the medium/cells can fall back into the tank again (symbolized on FIG. 4 by arrows 20).

During operation, evaporation occurs, reducing the culture volume and concentrating different compounds in the medium, which could be detrimental to the cells. To avoid these problems, it is possible to add devices such as condensers for exhaust gas or humidifiers for gas supply. Moreover, it is possible to connect more inlet and/or outlet tubing to the column, it can be useful, for instance, for acids, bases, antifoam or elicitation solutions adding. Optional devices can be added to this culture system for control and/or regulation of culture conditions such as (but not limited to) thermometer, pH meter, gas evaluation systems, cell density, pressure control, and mass control . . . It is also possible to place a light generator apparatus around the bioreactor for photoautotrophic plant cells for example. Regulation of temperature in the bioreactor can be achieved by different systems such as (but not limited to) placing the bioreactor in a room where temperature is controlled via suitable air conditioning, using jacketed outer containers where a circulation of temperature regulated water or air is provided, or any other means known by the skilled person.

The present invention is based on the fact that liquid culture trickles between the rising gas-bubble (6) and the sidewalls of the bioreactor (as shown by arrows (14) in FIG. 1). This results in vortices (15) to mix the bulk, avoiding cells to settle and in a thin liquid film (16) in contact with gas bubbles (6) where mass transfer is easily achieved for aeration.

This culture system is easy to operate since user can choose the volume and the frequency of bubbles by programming the bubble generator as previously described.

The system of the invention can be used to grow living cells, such as for example plant cells, animal cells, or microorganisms such as yeast cells, for example. Said cells can produce, for example, biomass cells, embryogenic plant cells, metabolites, secondary plant metabolites, and/or recombinant molecules.

EXAMPLE

The following example is illustrative of some of the products and methods of making the same falling within the scope of the present invention. It is not to be considered in any way limitative of the invention. Changes and modifications can be made with respect to the invention. That is, the skilled person will recognise many variations in this example to cover a wide range of formulas, ingredients, processing, and mixtures to rationally adjust the naturally occurring levels of the compounds of the invention for a variety of applications.

Example

Comparison of Growth with Soya Cell Cultures

The ability of the invention to grow Soya cells has been demonstrated using batch cultures. This is comparable or better than in Erlenmeyer flask or stirred tank bioreactor, even at larger scale.

Tissue culture strains of Glycine max (L.) Merr. were initiated from different cultivars on Gamborg et al. medium (1968) supplemented with 20 g.L$^{-1}$ sucrose, 7 g.L$^{-1}$ agar (bacto-agar Difco) and 1 mg.L$^{-1}$ 2,4-Dichlorophenoxyacetic acid. The pH is adjusted to 5.8 prior autoclaving (30 min at 115° C.). One strain (13406, cv. Maple arrow) was transferred in liquid medium (same medium as for tissue cultures without agar and 30 g.L$^{-1}$ sucrose) and subcultured in 250 mL Erlenmeyer flask (3 g.L$^{-1}$ fresh weight with 100 mL medium) every two weeks, in the same conditions than tissue culture collection. The Erlenmeyer flasks were placed on an orbital shaker at 100 rpm (shaking diameter 20 mm).

A 14 L stirred tank bioreactor (New Brunswick Scientific) with two six flat blade impellers, was used with the same medium and conditions of temperature and pH as mentioned above. The bioreactor containing 9 L of fresh medium was autoclaved 40 min at 115° C. Fourteen day old Soya cells were filtered from two 1 L Erlenmeyer flasks (500 ml medium). 300 g fresh weight was put into 1 L of fresh medium in a sterile tank with a specific output to be connected aseptically to the bioreactor for inoculation. The stirrer speed was adjusted at 100 rpm. Dissolved oxygen was maintained at 30% by increasing or decreasing air flow rate, using a biocontroller equipped with a sterilizable oxygen probe (Ingold), and a mass flowmeter A 25 L Cell culture system called large bubble column (as previously described), putted into a rigid outer container, was filled with 20 L of Soya cells in fresh culture medium (30 g/L fresh weight). Temperature of the room was regulated at 25° C. and a 12 cm diameter bubble (about 10 cm height) was generated every 5 seconds (by programming the bubble generator as mentioned above).

Growth measurements: Samples of cultivation bulk were taken at certain periods of growth from flasks, stirred tank bioreactor and large bubble column and sample volume was measured. Cells were then removed from liquid culture via filtration. Biomass was weighed (fresh weight). An aliquot of this biomass (about 1 g) was weighed precisely and putted into a drying room at 100° C. during 24 hours and then weighed precisely again (dry weight).

This example shows that the 20 L scale column provides a gentle environment to the cells, comparable with flasks and better than the stirred tank reactor. Cell damages are limited and mass and gas transfers are efficient in the operated conditions.

As already mentioned above, the present invention provides numerous advantages, which in turn are keys to economic benefits:

It provides a gentle environment to grow plant cells
Scale-up is easy
It is disposable
It is easy to operate

The invention claimed is:

1. Bioreactor for culturing living cells in a liquid medium comprising:
    at least one stationary plastic bag enclosing the cells and liquid culture medium, and
    at least one means for introducing single large gas bubbles at a bottom of the vessel, the single large bubble width from 50 to 99% of the tank width.

2. Bioreactor for culturing living cells in a liquid medium comprising:
    at least one stationary tank enclosing the cells and liquid culture medium, and
    at least one means for introducing single large gas bubbles at a bottom of the vessel, the single large bubble width at least 98.5% of the tank width.

3. Bioreactor for culturing living cells in a liquid medium comprising:
    at least one stationary flexible plastic bag enclosing the cells and liquid culture medium, and
    at least one means for introducing single large gas bubbles at a bottom of the vessel, the single large bubble width from 50 to 99% of the tank width.

4. Bioreactor for culturing living cells in a liquid medium comprising:
    at least one stationary tank enclosing the cells and liquid culture medium, and
    at least one means for introducing single large gas bubbles at a bottom of the vessel, the single large bubble width from 60% to 99% of the tank width.

5. Bioreactor for culturing living cells in a liquid medium comprising:
    at least one stationary tank enclosing the cells and liquid culture medium, and
    at least one means for introducing single large gas bubbles at a bottom of the vessel,
    the single large bubble width from 50 to 99% of the tank width, wherein the upper part of the tank is flared and wherein the stationary tank is surrounded by a rigid outside container.

* * * * *